(12) United States Patent
Haberkorn

(10) Patent No.: US 8,793,083 B2
(45) Date of Patent: Jul. 29, 2014

(54) DEVICE FOR PROCESSING TISSUE SAMPLES

(75) Inventor: Claus Haberkorn, Dielheim (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 624 days.

(21) Appl. No.: 12/903,719

(22) Filed: Oct. 13, 2010

(65) Prior Publication Data

US 2011/0087448 A1 Apr. 14, 2011

(30) Foreign Application Priority Data

Oct. 14, 2009 (DE) .......................... 10 2009 049 375

(51) Int. Cl.
*G01F 17/00* (2006.01)

(52) U.S. Cl.
USPC .................................. 702/55; 702/33; 702/50

(58) Field of Classification Search
USPC .............. 702/33, 50, 55; 427/2.11, 8; 422/50, 422/68.1
See application file for complete search history.

(56) References Cited

U.S. PATENT DOCUMENTS

| 3,526,203 | A | 9/1970 | Kinney et al. |
| 5,560,956 | A | 10/1996 | Schmehl |
| 8,233,953 | B2 * | 7/2012 | Colvin, Jr. .................... 600/316 |
| 8,257,968 | B2 * | 9/2012 | Sweet et al. ............... 435/288.7 |
| 2007/0125170 | A1 | 6/2007 | Tenney |
| 2008/0220468 | A1 | 9/2008 | Windeyer et al. |

FOREIGN PATENT DOCUMENTS

| JP | S59183333 A | 10/1984 |
| JP | H06120193 A | 4/1994 |
| JP | 2001-194276 A | 7/2001 |
| JP | 2001194276 A | 7/2001 |
| JP | 2005504323 A | 2/2005 |
| WO | 03/029845 A2 | 4/2003 |
| WO | 03029845 A2 | 4/2003 |
| WO | 2005/031312 A1 | 4/2005 |

* cited by examiner

*Primary Examiner* — Elias Desta
(74) *Attorney, Agent, or Firm* — Hodgson Russ LLP

(57) ABSTRACT

A device (20) for processing tissue samples has a processing room (22) for introducing and processing the tissue samples (20). A chamber (34) communicates with the processing room (22). At least one filling level sensor (28, 30, 32) detects a measurement value which is representative of a filling level of a liquid in the chamber (34). A calculating unit determines a filling level of the liquid in the processing room (22) depending on the filling level of the liquid in the chamber (34).

19 Claims, 2 Drawing Sheets

DEVICE FOR PROCESSING TISSUE SAMPLES

CROSS REFERENCE TO RELATED APPLICATIONS

This application claims priority of German patent application number 10 2009 049 375.1 filed Oct. 14, 2009, the entire disclosure of which is incorporated by reference herein.

FIELD OF THE INVENTION

The invention relates to a device for processing tissue samples. The device has a processing room for introducing and processing the tissue samples.

BACKGROUND OF THE INVENTION

Samples, in particular tissue samples, are usually processed with reagents and then cut into thin sections so that they can be examined with the aid of a microscope. The tissue samples are processed semi or fully automatically preferably in a tissue processor and in particular are successively exposed to the various reagents. In this process, the tissue samples are introduced into a device for processing tissue samples, in particular a retort. Thereafter, the retort is successively filled with the various reagents for clearing, dehydrating and fixing of the tissue samples so that the tissue samples are exposed to the respective reagents. In almost every process step it is important that the tissue samples are completely covered with reagent and thus are completely exposed to the respective reagent. For this reason, filling level sensors are usually arranged in retorts. These may be damaged by cleaning tools or baskets for receiving tissue samples. Further, filling level measurements may be skewed by the baskets.

JP 2001194276 A shows a tissue processor comprising a processing room which communicates with a chamber in which a filling level sensor is arranged. The filling level sensor comprises an ultrasonic transmitter and an ultrasonic receiver which are each arranged at different sides of the chamber.

From U.S. Pat. No. 3,526,203, a tissue processor for fixing, dehydrating and clearing tissue samples is known. For receiving the tissue samples, the tissue processor has a processing chamber which communicates with containers in which reagents are stored. Liquid control units are provided with the aid of which predetermined amounts of reagents can be supplied to the processing chamber.

A further tissue processor is described in US 2008/0220468 A1. The tissue processor comprises two retorts, wax baths, reagent containers, a pump and a valve. With the aid of the valve, the reception of the reagents into a processing room of the tissue processor is controlled. Filling level sensors are arranged in a wall of the processing room.

U.S. Pat. No. 5,560,956 A shows a tissue processor comprising a process chamber and at least one reservoir for receiving a processing reagent. Means are provided with the aid of which reagents are driven from the reservoir to an auxiliary reservoir and from the auxiliary reservoir to the process chamber.

SUMMARY OF THE INVENTION

It is the object of the invention to specify a device for processing tissue samples in which a filling level of a liquid in a processing room of the device can be detected particularly precisely.

The object is solved by the features of the independent claims. Advantageous embodiments are specified in the subclaims.

According to a first aspect, the invention is characterized by a chamber which communicates with the processing room. At least one filling level sensor for detecting a measurement value is provided which is representative of a filling level of a liquid in the chamber. Depending on the filling level of the liquid in the chamber, a calculating unit determines a filling level of the liquid in the processing room.

The fact that the filling level sensor detects the filling level in the chamber, which level is representative of the filling level of the liquid in the processing room, makes it possible to arrange the filling level sensor outside of the processing room, in particular with its sensitive area in the chamber. This helps that the measurement is not skewed by objects in the processing room, such as baskets with tissue samples, and/or that during cleaning of the processing room or during exchange of the baskets the filling level sensor is not damaged. As a result thereof, the filling level in the processing room can be determined particularly precisely. The device for processing tissue samples can also be referred to as retort.

The chamber is formed in a wall of the processing room and separated from the processing room by a perforated sheet. By forming the chamber in the wall, it can easily be guaranteed that there is the same filling level in the chamber as in the processing room, which inter alia helps that the filling level in the processing room is determined particularly easily. The perforated sheet, in addition to the chamber, contributes to the protection of the filling level sensor and, at the same time, guarantees that there is the same filling level in the chamber as in the processing room.

According to a second aspect, the invention is characterized in that the filling level sensor is installed such that a longitudinal axis of the filling level sensor encloses a predetermined angle which is greater than 0° and smaller than 90° with the wall of the processing room. By the inclined installation of the filling level sensor according to the predetermined angle, a travel of a sensor signal between a sensitive tip of the filling level sensor and a basket arranged in the processing room is increased so that when a basket is introduced into the retort, the basket skews the measurement of the filling level only negligibly or not at all. The predetermined angle is, for example, greater than 50° and smaller than 60°, in particular 55°.

According to a third aspect, the invention is characterized by a heating device for heating the filling level sensor. This helps that in the sensitive area of the filling level sensor no condensate forms by which the measurement of the filling level might be skewed. In this connection it is particularly advantageous when the heating device is arranged in a recess of a wall of the processing room.

In an advantageous development, the heating device comprises a first heating element which is arranged above the filling level sensor and/or a second heating element which is arranged below the filling level sensor. If several filling level sensors are provided then for each of the filling level sensors one and/or two heating elements each are provided. The heating elements can, for example, be heating rods in which heating coils are formed. The heating rods can then, for example, be inserted into bores in the wall.

So that a different number of baskets with tissue samples can be arranged on top of one another in the processing room, and nevertheless an economical filling of the processing room is possible, in an advantageous development of one or more of the three aspects at least one filling level sensor each is provided for each layer of baskets, in particular in an advantageous development at least three filling level sensors are arranged on top of one another. In order to avoid overfilling of the processing room, it is advantageous to provide on top of the three filling level sensors at least a fourth filling level sensor serving as a safety sensor.

It is particularly advantageous when the first and the second aspect are combined with one another and the filling level sensor detects the filling level in the chamber and is arranged at the predetermined angle to the wall of the processing room. Alternatively or additionally, the second and the third aspect can be combined with one another and the filling level sensor can be arranged at the predetermined angle to the wall of the processing room and can be heated with the aid of the heating device. Alternatively or additionally, the first and the third aspect can be combined with one another and the filling level sensor can detect the filling level in the chamber and can be heated with the aid of the heating device. An almost optimum measurement of the filling level is achieved when all three aspects are combined with one another and the filling level sensor detects the filling level in the chamber and the filling level sensor is arranged at the predetermined angle to the wall of the processing room and is heated with the aid of the heating device.

BRIEF DESCRIPTION OF THE DRAWING VIEWS

In the following, the invention will be explained in more detail with reference to schematic drawings.

DETAILED DESCRIPTION OF THE INVENTION

Elements having the same structure or function are identified with the same reference signs throughout all Figures.

Figure 1:
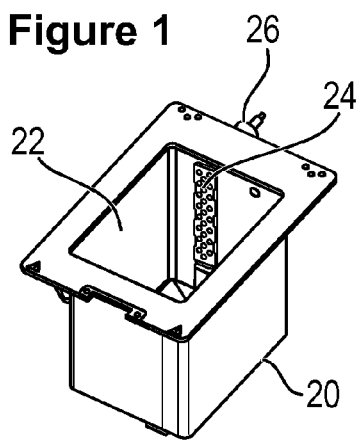
FIG. 1 shows a device for processing tissue samples.

FIG. 1 shows a device 20 for processing tissue samples. The device 20 can also be referred to as retort. Preferably, the retort is arranged in a tissue processor. The retort serves to receive tissue samples and to treat them with one or more liquids, in particular reagents and/or process media. For this, the retort has a processing room 22 and one or more inlets and outlets via which the liquids can be filled into the processing room 22 of the retort. Further, the retort has a non-illustrated cover plate so that the retort can be closed during processing of the tissue samples. In addition to the processing room 22, the retort comprises a cover 24 and an uppermost filling level sensor 26. The cover 24 is formed by a perforated sheet. The uppermost filling level sensor 26 serves as a safety sensor which helps that the retort is not overfilled. The liquids comprise, for example, preservatives, various alcohols or liquefied wax-like reagents such as liquid paraffin.

Figure 2:
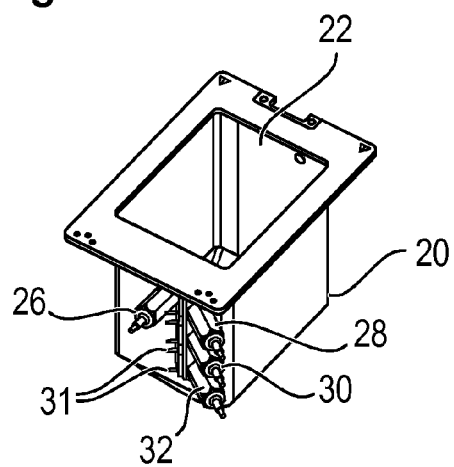
FIG. 2 shows a second view of the device.

FIG. 2 shows the retort according to FIG. 1 in a rear view and in particular a first filling level sensor 28, a second filling level sensor 30 and a third filling level sensor 32. For each of the filling level sensors 28, 30, 32, two heating devices 31 each are provided. The filling level sensors 26, 28, 30, 32 have sensitive areas which project into the chamber 34. Alternatively, the sensitive areas can border on the chamber 34. The filling level sensors 26, 28, 30, 32 have longitudinal axes which lie in horizontal planes which are parallel to one another. In this embodiment, the filling level sensors 26, 28, 30, 32 are optical sensors which comprise as a sensitive area one glass lens each through which a laser beams passes during operation. Radiation reflected by the surrounding, for example, by the liquid in the processing room passes through the glass lens and is detected with a light-sensitive sensor element. Alternatively, for example also acoustically operating sensor elements, such as ultrasound sensors, can be arranged.

Figure 3:
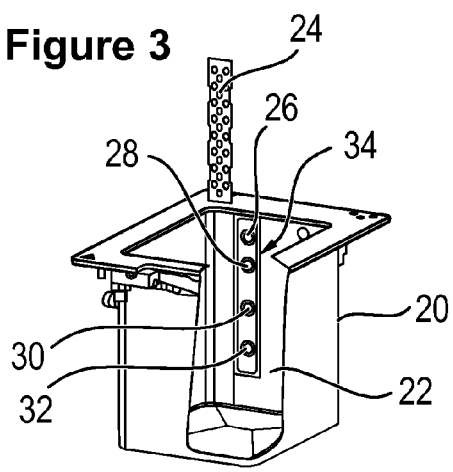
FIG. 3 shows a partial section of the device with a cover removed.

FIG. 3 shows a partial section of the retort so that an interior view of the processing room 22 can be seen. Under the cover 24, which is removed in this illustration, there is a chamber 34. Sensor surfaces, in particular the sensitive areas of the filling level sensors 28, 30, 32 and 26 project into the chamber 34. The chamber 34 is formed by the wall of the processing room 22. One side of the chamber 34 is completely open to the processing room 22 and during operation of the tissue processor separated from the processing room 22 by the cover 24 such that the liquid in the processing room 22 enters the chamber 34. The chamber 34 helps that the filling level sensors 26, 28, 30, 32 are not damaged by a cleaning process, in particular by cleaning tools or by introducing and removing tissue samples. This protective action is increased by the cover 24.

The chamber 34 communicates with the processing room 22 so that the liquid flows from the processing room 22 into the chamber 34. The filling level sensors 28, 30, 32 detect a measurement value which is representative of the filling level in the chamber 34. Depending on the measurement value, a non-illustrated calculating unit then determines the filling level in the chamber 34 and, depending thereon, the filling level in the processing room 22. In the illustrated embodiment, the filling level in the chamber 34 always corresponds to the filling level in the processing room 22.

Figure 4:
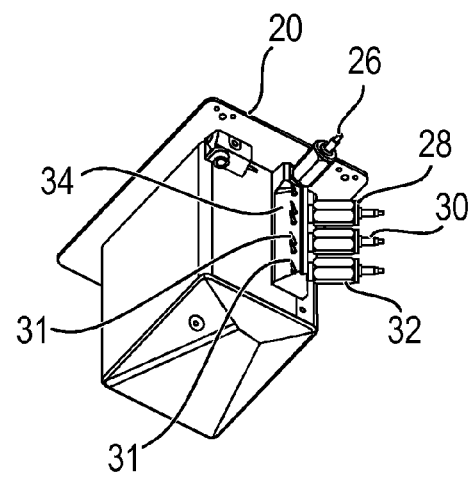
FIG. 4 shows a third view of the device.

FIG. 4 shows the rear view of the retort according to FIG. 2 from below and in particular an outside of the chamber 34. From FIGS. 2 and 4 it results that the longitudinal axes of the filling level sensors 28, 30, 32 enclose a predetermined angle with a wall of the processing room 22. The predetermined angle is 55°. Installing the filling level sensors 28, 30, 32 at the predetermined angle relative to the wall, increases the path of a sensor signal, in particular a laser beam, between a sensitive area of the filling level sensors 28, 30, 32 and tissue samples arranged in the processing room 22. This helps that the measurement of the filling level is skewed by reflections on the tissue samples only negligibly or not at all, in particular in the case of optically operating filling level sensors 26, 28, 30, 32.

Figure 5:
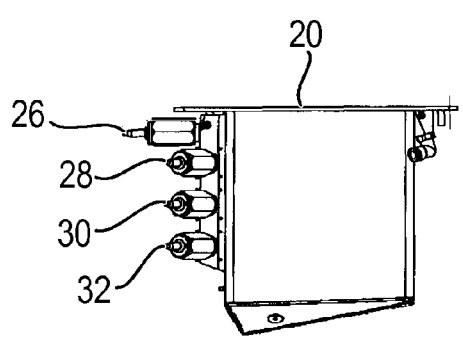
FIG. 5 shows a side view of the device.
Figure 6:
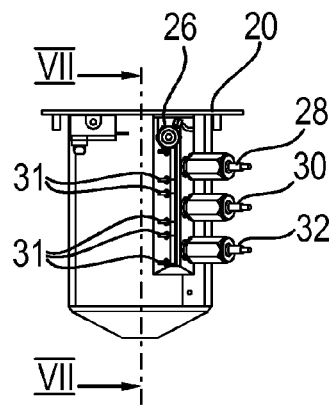
FIG. 6 shows a rear view of the device.

FIG. 5 shows a side view of the retort and FIG. 6 shows a rear view of the retort, from which it can be particularly well seen that the heating device 31 comprises several heating elements, in particular heating cartridges which are arranged above and below one of the filling level sensors 20, 30, 32 each. The heating device 31 heats via a wall of the chamber 34 the filling level sensors 26, 28, 30, 32, in particular the glass lenses, and thus prevents condensation of liquid on the filling level sensors 26, 28, 30, 32. This helps to precisely measure the filling level.

Figure 7:
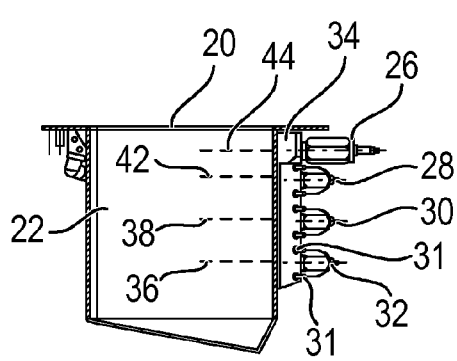
FIG. 7 shows a cross-section of the device according to FIG. 6.

FIG. 7 shows a cross-section of the retort according to FIG. 6. The filling levels which can be checked by means of the individual filling level sensors 28, 30, 32 are indicated by broken lines. In particular, an upper filling line 42 is assigned to the first filling level sensor 28, a center filling line 38 is assigned to the second sensor 30 and a lower filling line 36 is assigned to the third filling level sensor 32. Further, a maximum filling level 44 which is to be checked with the uppermost filling level sensor 26 is indicated in broken lines.

Figure 8:
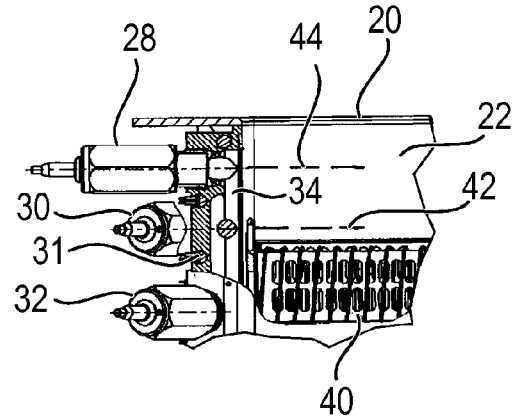
FIG. 8 shows a detailed view of the device according to FIG. 7.

FIG. 8 shows a detailed view of a portion of an upper part of the retort. In the processing room 22, a basket 40 with tissue samples is arranged. Further, FIG. 8 shows the electric connections of the heating device 31 which, in this embodiment, comprises for each of the filling level sensors 28, 30, 32 two heating elements, in particular one upper heating rod and one lower heating rod each, which are arranged in bores of the wall of the chamber 34. In particular, the heating devices 31 are arranged such that they heat the wall of the chamber 34.

The filling lines 36, 38, 42 are arranged such that the lowermost filling line 36 extends slightly above the upper edge of a lowermost basket 40 and the center filling line 38 extends slightly above a center basket 40 and the uppermost filling line 42 extends slightly above an uppermost basket 40. This allows to exactly check, depending on the number of baskets 40, the filling level required.

The invention is not restricted to the embodiment as described. For example, the retort can have no chamber 34, the filling level sensors 26, 28, 30, 32 then being arranged outside of the chamber 34 at the predetermined angle and/or are heated with the heating device 31. Further, the first to third filling level sensors 28, 30, 32 can be arranged perpendicular to the wall in the chamber 34 in correspondence with the uppermost filling level sensor 26. Alternatively to the perforated sheet used as a cover 24, also another separation can be provided between the chamber 34 and the processing room 22 which allows for a communication between the chamber 34 and the processing room 22, for example, a sheet with a vertical longitudinal slot. Further, also more or less filling level sensors 26, 28, 30, 32 can alternatively be provided. Alternatively, also the predetermined angle can deviate from the 55° and, for example, lie between 50° or 60° or enclose another angle with the wall of the processing room 22. Further, the chamber 34 can be spaced from the processing room 22 and communicate therewith via a liquid line. In this case, the filling level in the chamber 34 does not have to correspond to the filling level in the processing room 22, the filling level in the processing room 22 then being determined by the calculating unit depending on the filling level in the chamber 34. For this, for example, an empirically determined allocation rule can be stored on a storage medium of the calculating unit.

LIST OF REFERENCE SIGNS

20 retort
22 processing room
24 cover
26 uppermost filling level sensor
28 first filling level sensor
30 second filling level sensor
31 heating device
32 third filling level sensor
34 chamber
36 lowermost filling line
38 center filling line
40 basket
42 upper filling line
44 maximum filling level

What is claimed is:

1. A device for processing tissue samples, comprising:
   a processing room for introducing and processing the tissue samples;
   a chamber in communication with the processing room;
   a filling level sensor for detecting a measurement value which is representative of a filling level of a liquid in the chamber; and
   a calculating unit that determines a filling level of the liquid in the processing room depending on the filling level of the liquid in the chamber;
   wherein the chamber is formed in a wall of the processing room and the chamber is separated from the processing room by a perforated sheet.

2. The device according to claim 1, wherein the filling level sensor is arranged in the chamber.

3. The device according to claim 2, further comprising a heating device arranged to heat the filling level sensor.

4. The device according to claim 2, wherein the filling level sensor has a longitudinal axis which encloses a predetermined angle of less than 90° with the wall of the processing room.

5. The device according to claim 3, wherein the filling level sensor has a longitudinal axis which encloses a predetermined angle of less than 90° with the wall of the processing room.

6. The device according to claim 1, wherein at least three filling level sensors are arranged on top of one another.

7. The device according to claim 6, wherein at least four filling level sensors are arranged on top of one another, wherein an uppermost filling level sensor is a safety sensor for avoiding overfilling of the processing room.

8. A device for processing tissue samples, comprising:
   a processing room for introducing and processing the tissue samples; and
   a filling level sensor for detecting the filling level of a liquid in the processing room, the filling level sensor having a longitudinal axis which encloses a predetermined angle of greater than 0° and less than 90° with a wall of the processing room, wherein the filling level sensor is arranged in the processing room.

9. The device according to claim 8, wherein the predetermined angle is greater than 50° and smaller than 60°.

10. The device for processing tissue samples according to claim 8, further comprising a heating device arranged to heat the filling level sensor.

11. The device according to claim 8, wherein at least three filling level sensors are arranged on top of one another.

12. The device according to claim 11, wherein at least four filling level sensors are arranged on top of one another, wherein an uppermost filling level sensor is a safety sensor for avoiding overfilling of the processing room.

13. A device for processing tissue samples, comprising:
   a processing room for introducing and processing the tissue samples;
   a filling level sensor, the measurement value of which is representative of a filling level of a liquid in the processing room; and
   a heating device configured to heat the filling level sensor for removing condensation from the filling level sensor, wherein the heating device is arranged in a recess of a wall of the processing room.

14. The device according to claim 13, wherein the heating device includes a heating element arranged above the filling level sensor.

15. The device according to claim 13, wherein the heating device includes a heating element arranged below the filling level sensor.

16. The device according to claim 13, wherein the heating device includes a first heating element arranged above the filling level sensor and a second heating element arranged below the filling level sensor.

17. The device for processing tissue samples according to claim 13, further comprising a chamber formed in a wall of the processing room, wherein the filling level sensor is arranged in the chamber and has a longitudinal axis which encloses a predetermined angle of less than 90° with the wall of the processing room.

18. The device according to claim 13, wherein at least three filling level sensors are arranged on top of one another.

19. The device according to claim 18, wherein at least four filling level sensors are arranged on top of one another, wherein an uppermost filling level sensor is a safety sensor for avoiding overfilling of the processing room.

\* \* \* \* \*